(12) United States Patent
Ng et al.

(10) Patent No.: US 6,720,285 B2
(45) Date of Patent: Apr. 13, 2004

(54) MATERIALS COMPRISING SACCHARIDE CROSS-LINKED AND CHEMICALLY BONDED TO A SUPPORT VIA UREA LINKAGES

(75) Inventors: Siu Choon Ng, Singapore (SG); Chi Bun Ching, Singapore (SG); Lifeng Zhang, Singapore (SG); Lei Chen, Singapore (SG)

(73) Assignee: National University of Singapore, Singapore (SG)

( * ) Notice: Subject to any disclaimer, the term of this patent is extended or adjusted under 35 U.S.C. 154(b) by 228 days.

(21) Appl. No.: 09/888,088

(22) Filed: Jun. 22, 2001

(65) Prior Publication Data

US 2002/0058588 A1 May 16, 2002

(51) Int. Cl.$^7$ ............................................ B01J 20/00
(52) U.S. Cl. .................................................. 502/404
(58) Field of Search .............................. 502/401, 404, 502/405, 415; 210/198.2

(56) References Cited

U.S. PATENT DOCUMENTS

| | | | |
|---|---|---|---|
| 4,539,399 A | 9/1985 | Armstrong | 536/103 |
| 5,104,547 A | 4/1992 | Cabrera et al. | 210/656 |
| 5,208,316 A | 5/1993 | Yoshinaga | 528/68 |
| 5,241,059 A | 8/1993 | Yoshinaga | 536/4.1 |
| 5,639,824 A | 6/1997 | Okamoto | 525/54.2 |
| 6,017,458 A | 1/2000 | Ng et al. | 210/635 |

OTHER PUBLICATIONS

Willie L. Hinze, "Applications of Cyclodextrins in Chromatographic Separations and Purification Methods", *Separation and Purification Methods*, 1981, 10(2), 159–237.

Y. Kawaguchi, et al., "Chemically Bonded Cyclodextrin Stationary Phases for Liquid Chromatographic Separation of Aromatic Compounds", *Anal. Chem.*, 1983, vol. 55, pp. 1852–1857.

D. W. Armstrong, et al., "Liquid Chromatographic Separation of Diastereomers and Structural Isomers on Cyclodextrin–Bonded Phases", *Anal. Chem.*, 1985, vol. 57, pp. 234–237.

Song Li, et al., "Cyclodextrins and Their Applications in Analytical Chemistry", *Chem. Rev.*, 1992, vol. 92, pp. 1457–1470.

D.W. Armstrong, et al., "Derivatized Cyclodextrins for Normal–Phase Liquid Chromatographic Separation of Enantiomers", *Anal. Chem.*, 1990, vol. 62, pp. 1610–1615.

Tihamer Hargitai et al., "Preparation and Chromatographic evaluation of 3,5–dimethylphenyl carbamoylated β– cyclodextrin stationary phases for normal–phase high–performance liquid chromatographic separation of enantiomers", *Journal of Chromatography*, 1993, vol. 628, pp. 11–22.

Tihamer Hargitai et al., "Evaluation of 3,5–Dimethylphenyl Carbamoylated α–, β–, and γ–Cyclodextrins as Chiral Stationary Phases for HPLC", *Journal of Liquid Chromatography*, 1993, vol. 16(4), pp. 843–858.

V. Schurig et al, "Enantiomer separation on a Chirasil–Dex–polymer–coated stationary phase by conventional and micro–packed high–performance liquid chromatography", *Journal of Chromatography A*, 1996, vol. 755, pp. 299–307.

Volker Schurig et al, "Toward Unified Enantioselective Chromatography with a Single Capillary Column Coated with Chirasil–Dex", *Angew. Chem. Int. Ed. Engl.*, 1994, vol. 33, No. 21, pp. 2222–2223.

Boris I. Gorin et al., "Efficient Perfacial Derivatization of Cyclodextrins at the Primary Face", *Tetrahedron Letters*, 1996, vol. 37, No. 27, pp. 4647–4650.

David Alker et al., "Per–6–bromo–per–2,3–dimethyl–β–cyclodextrin", *Tetrahedron Letters*, 1994, vol. 35, No. 48, pp. 9091–9094.

Christine Roehoi–Stoeckel et al., "A simple Synthesis of a Highly Water Soluble Symmetrical β–Cyclodextrin Derivative", *Tetrahedron Letters*, 1997 vol. 38 No. 9, pp. 1551–1554.

Li–Feng Zhang et al., "A facile route into $6^A$–mono–ω–alkenylcarbamido–$6^A$–deoxy–perfunctionalised cyclodextrin:key intermediate for further reactive functionalisations", *Tetrahedron: Asymmetry*, 10 (1999), pp. 4107–4113.

Li–Feng Zhang et al., "A facile Immobilisation Approach for Perfunctionalised Cyclodextrin onto Silica via the Staudinger Reaction", *Tetrahedron Letters* (1999), 40, pp. 1815–1818.

Primary Examiner—Stanley S. Silverman
Assistant Examiner—Edward M. Johnson
(74) Attorney, Agent, or Firm—Klarquist Sparkman, LLP

(57) ABSTRACT

A conjugate of a support material and an oligomer or polymer of a saccharide that is linked to the support material via urea linkages, and in which the oligomers or polymers are cross-linked via urea linkages provides a valuable stationary phase for chromatography. It is particularly valuable as a chiral stationary phase in enantiomeric separations and enantiomeric analysis.

23 Claims, 2 Drawing Sheets

Figure 1: synthesis procedure of present invention. R= H, alkyl, aryl, ester or carbamate
Showing only step (a).

MATERIALS COMPRISING SACCHARIDE CROSS-LINKED AND CHEMICALLY BONDED TO A SUPPORT VIA UREA LINKAGES

FIELD OF THE INVENTION

The present invention relates to the development of novel materials that can be used in a process such as high performance liquid chromatography (HPLC), liquid chromatography (LC), thin layer chromatography (TLC), capillary electro chromatography (CEC) and counter-current chromatography. The materials are composed of support materials and saccharide moieties, especially glucose moieties preferably in the form of cyclodextrins, mutually cross-linked and chemically bonded via urea linkages. The invention further relates to processes for the production of these materials and their use in separating compounds and especially resolving enantiomeric mixtures.

BACKGROUND OF THE INVENTION

Generic applicability of cyclodextrins in chromatographic separation and purification processes is described at length in reviews by W. L. Hinze, *Separation and purification methods*, 1981, 10(2), 159–237. Y. Kawaguchi, et al., *Anal. Chem.*, 1983, 55, 1852; D. W. Armstrong, et al., *Anal. Chem.*, 1985, 57, 234 and S. Li, et al., *Chem. Rev.*, 1992, 92, 1457. Chromatographic separation on chiral stationary phases (CSP) is also the most convenient analytical method for the determination of enantiomeric purity (see for example S. G. Allenmark, *Chromatographic Enantioseparations: Methods and Applications*, $2^{nd}$ ed., Prentice Hall, N.J., 1991). In recent years, tremendous research efforts were made in bonding cyclodextrins to solid matrices, such as silica gel, via amino or amido linkages. However, these bonds are inherently unstable to hydrolysis, thus placing severe limitations on use of these materials in aqueous media. Alternative approaches for immobilizing cyclodextrin using hydrolytically more stable ether linkages (U.S. Pat. No. 4,539,399) or carbamic acid moieties (U.S. Pat. No. 5,104,547) were also investigated. However, in all these approaches, regioselective derivatisation of cyclodextrin cannot be readily effected due to the presence of multiple hydroxy moieties in the cyclodextrin starting materials. Thus, reaction may take place on the 2, 3 or 6-position of glucose moieties of cyclodextrin, which is hard to resolve.

It has been reported that derivatised cyclodextrin stationary phases for liquid chromatography show definite enantioselectivity for a variety of compounds while pristine cyclodextrin bonded stationary phases display low enantioselectivity. Enantioselectivity of the materials was generally improved by increasing the degree of derivatisation of the —OH groups on cyclodextrin with carbamate groups, and by increasing the surface concentration of cyclodextrin immobilized on the support materials (D. W. Armstrong et al., *Anal. Chem.*, 1990, 62, 1610; T. Hargitai et al., *J. Chromatogr.*, 1993, 628, 11; T. Hargitai, et al., *J. Liq. Chromatogr.*, 1993, 16(4), 843). In order to maximize the extent of cyclodextrin derivatisation, large molar excesses of derivatising reagents under vigorous conditions were often used. However, the derivatisation processes invariably involved the prior immobilisation of underivatised cyclodextrin on the support material followed by derivatisation procedures involving solid-liquid phases. This usually results in partial derivatisation of the hydroxyl groups of the cyclodextrin and also in large, sterically encumbered cyclodextrins having a low extent of derivatisation. These methods did not give good reproducibility or uniformity of product, with the consequence that separation of enantiomers may vary from batch to batch of the obtained CD-based CSP.

Ng, et al., U.S. Pat. No. 6,017,458 describe a procedure of immobilizing perfunctionalized cyclodextrin onto the surface of a support. The patent says that the cyclodextrin is immobilized via a urethane linkage, but it is believed that this is not correct and the linkage is a urea linkage. The procedure provides an efficient method with well-defined chemical structure and very good reproducibility. However, in these examples, and in the other instances listed above, the cyclodextrins were immobilized onto the support as small molecules, which potentially limit their stability in mobile phases with high aqueous content. Although the patent mentions monoazido and diazido cyclodextrins, only monoazido cyclodextrins are used in the examples of the patent and each immobilized cyclodextrin will have only one urea linkage linking it to the support material.

Polysiloxane with cyclodextrin anchored to its side chain has been prepared and coated onto the surface of silica gel. This material exhibits interesting properties in reverse phase HPLC. (V. Schurig, et al., *J. Chromatogr. A*, 1996, 755, 299; V. Schurig, et al., Ger Offen DE 43 24 636 A1 (1994), V. Schurig, et al., *Angew. Chem. Int. Ed. Engl.*, 1994, 33, 2222). However, there is no report of the cyclodextrin polymer immobilized onto a support and applied in chiral separation.

SUMMARY OF THE INVENTION

In one aspect the invention provides a conjugate comprising a support material linked to oligomers or polymers of a saccharide which linking is via urea linkages between the saccharide moieties and the support material, and wherein the oligomers or polymers of the saccharide are also cross-linked via urea linkages.

In another aspect the invention provides a process for preparing a conjugate of the invention, which process comprises: (a) reacting an oligomer or polymer of a saccharide bearing a plurality of azide groups with an amine, preferably a primary amine, a phosphine and $CO_2$, the amine being on the surface of a support material; or (b) reacting an oligomer or polymer of a saccharide bearing a plurality of azide groups with an amine, preferably a primary amine, a phosphine and $CO_2$, wherein the amine is an alkenylamine, subsequently hydrosilylating the alkenyl moiety of the product with a hydrosilylating agent that bears one or more readily hydrolysable groups on the silicon atom and thereafter reacting with a support member; or (c) reacting an oligomer or polymer of a saccharide bearing a plurality of azide groups with an amine, preferably a primary amine, a phosphine and $CO_2$, wherein the amine is present in a molecule that bears a silicon atom bearing at least one readily hydrolysable group, and thereafter reacting with a support member; or (d) reacting an oligomer or polymer of a saccharide bearing a plurality of amine groups, preferably primary amine groups, with an azide group, a phosphine and $CO_2$, the azide group being on the surface of a support material; or (e) reacting an oligomer or polymer of a saccharide bearing a plurality of amine groups, preferably primary amine groups, with an azide, a phosphine and $CO_2$, wherein the azide is an alkenylazide, subsequently hydrosilylating the alkenyl moiety of the product with a hydrosilylating agent that bears one or more readily hydrolysable groups on the silicon atom and thereafter reacting with a support member; or (f) reacting an oligomer or polymer of a saccharide bearing a plurality of amine groups, preferably primary amine groups, with an azide, a phosphine and $CO_2$, wherein the azide is present in a molecule that bears a silicon atom bearing at least one readily hydrolysable group, and thereafter reacting with a support member.

DESCRIPTION OF PREFERRED EMBODIMENTS

The present invention makes use of a Staudinger reaction, in which an azide group, an amine group, $CO_2$ and a phosphine react to form a urea. Azide groups can be present on the oligomer or polymer of a saccharide, and amine groups can be present on the support material, or on a molecule that will subsequently be linked to the support material, so that the saccharide is linked via urea to the support material. Alternatively, amine groups can be present on the oligomer or polymer of the saccharide, and the azide groups can be present on the support material, or on a molecule that will subsequently be linked to the support material, so that again the saccharide is linked via urea to the support material. It is preferred that the azide groups are on the saccharide and the amine groups are on the support material, or on a molecule that will subsequently be linked to the support material.

Saccharides normally contain one primary hydroxyl group and several secondary hydroxyl groups. In preferred embodiments of the process of the present invention there is used an oligomer or polymer of a saccharide in which the primary hydroxyl groups of the saccharide moieties have been replaced by azide groups. For instance, glucose bears a primary hydroxyl group on the 6-carbon atom and in a preferred embodiment of the present invention there is used an oligomer or polymer of glucose in which the primary hydroxyl groups of each glucose moiety have been replaced by azide groups on each 6-carbon atom. Thus, there is used an oligomer or polymer bearing a large number of azide groups, and reaction occurs at the large number of azide groups, creating a large number of urea linkages between the oligomer or polymer and the support material, and also a large number of urea cross-linkages between the oligomer and polymer. This enhances column stability, particularly when the conjugate of the invention is used as stationary phase in chromatography and the mobile phase has high water content.

The oligomer or polymer of a saccharide can be straight-chained, or cyclic. Examples of saccharides include glucose, fructose, mannose, galactose, ribose, arabinose, xylose, lyxose, erythrose and threose, of which glucose is preferred. The subsequent description is given with respect to glucose, and particularly with respect to cyclodextrins, but it should be understood that use of oligomers and polymers of saccharides other than glucose, and glucose other than in the form of cyclodextrins, are also within the scope of the invention. For the most part, the description is given with respect to saccharides that bear azide groups and support materials that bear amine groups but it should be understood that the invention extends to use of saccharides that bear amine groups and support materials that bear azide groups.

Most preferably a cyclic oligomer is used, especially α, β or γ cyclodextrin composed of six, seven or eight glucose moieties, respectively. Straight-chained oligomers and polymers can be used, however, and mention is made of cellulose, amylose and pullulan as materials that can serve as the saccharide-containing oligomer or polymer, once hydroxyl groups have been replaced by azide groups. They can be used in the form of their esters, for example cellulose acetate, provided that there are sufficient free hydroxyl groups to be converted to azide groups and thereafter to participate in the reaction to form the conjugate of the invention, as described below.

To prepare the conjugate of the invention there can be used a reactant that includes glucose moieties in which hydroxy groups at the 6-positons of the glucose moieties have been replaced by azide moieties. Use is made of a reaction in which the azide-bearing glucose moieties are reacted with an amine in the presence of carbon dioxide and a reactant that will participate in the Staudinger reaction, for example a trihydrocarbylphosphine, preferably triphenylphosphine, to form a urea. This is a facile one pot reaction that proceeds in high yield. To illustrate, if the reactant that contains glucose moieties is β-cyclodextrin, there is used a $6^A, 6^B, 6^C, 6^D, 6^E, 6^F, 6^G$-heptakisazido-$6^A, 6^B, 6^C, 6^D, 6^E, 6^F, 6^G$-heptakisdeoxy cyclodextrin.

The amine groups may be on the surface of a support material, or the amine groups may be on a molecule that bears another functional group. That other functional group is used to join the intermediate formed by reaction between the glucose and the amine to the support material.

The amine that reacts with the azide and $CO_2$ can be a primary or secondary amine. Primary amines are preferred and the further description refers only to primary amines.

The azide moieties can react with the amine groups on the support material and also with azide moieties on adjacent β-cyclodextrin molecules, so that each cyclodextrin becomes bound not only to the support material but also to adjacent cyclodextrin molecules. Preferably all, or substantially all, of the 6-carbon atoms of the glucose moieties bear azide moieties, so the cyclodextrin moieties are securely bound to each other and to the support.

Each oligomer or polymer of glucose is linked via a plurality of urea linkages i.e., more than two linkages per oligomer or polymer, and preferably more than six linkages per oligomer or polymer. Preferably there is a urea linkage for each glucose moiety present in the oligomer or polymer. For example, if the oligomer is β-cyclodextrin it is preferred that the 6-carbon atom of each of the seven glucose moieties that constitute β-cyclodextrin shall bear an azide group that will participate in a urea-forming reaction, so that each cyclodextrin is linked by up to seven urea linkages.

The 6-azido glucose moieties may bear hydroxyl groups at the 2- and 3-positions, or they may bear other functional groups or protecting groups. It is preferred that either all or none of the hydroxyl groups at the 2- and 3-positions are replaced by other functional groups or protecting groups, i.e., that the glucose is perfunctionalized or is pristine, respectively. Partially functionalized materials are within the scope of the invention, however.

As groups that can replace hydroxyl groups in the 2- and 3-positions there are mentioned alkoxy groups, aryloxy groups, acyloxy groups and carbamoyloxy groups. As examples of alkoxy groups there are mentioned straight-chained and branched alkyl groups having up to about 6 carbon atoms, especially ethyl and methyl, and cycloalkyl containing 5 or 6 carbon atoms. As examples of aryloxy groups there are mentioned phenoxy and α- and β-naphthyloxy groups. As acyloxy groups there are mentioned alkanoyloxy groups containing up to about 6 carbon atoms, especially acetyloxy. Carbamates can be, for example, phenylcarbamoyloxy or α- or β-naphthylcarbamoyloxy groups.

The reactant that includes glucose moieties bearing azide groups on the 6-carbon atoms can be obtained, for example, by halogenating the glucose moieties on the 6-carbon atoms and then replacing the halogen atoms with azide groups. Thereafter, if required, the glucose can be perfunctionalized. To illustrate the procedure of B. I. Gorin, *Tetrahedron Lett.*, 1996, 37(27), 4647; D. Alker, *Tetrahedron Lett.*, 1994, 35(48), 9091; C. Roehoi-Stoeckel, *Tetrahedron Lett.*, 1997 38(9), 1551; or Yoshinaga, U.S. Pat. No. 5,241,059 can be used to prepare cyclodextrins substituted by iodine or bromine atoms. (These articles are all incorporated by reference.) This is followed by reaction with an alkali metal azide, for example $NaN_3$, $LiN_3$ or $KN_3$, in a polar solvent, for example dimethylformamide (DMF). If required, the other hydroxyl groups on the 2- and 3-positions can thereafter be fully derivatised to give a perfunctionalized cyclodextrin.

A $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-acetyl-$3^A$, $3^B$, $3^C$, $3^D$, $3^E$, $3^F$, $3^G$-heptakis-O-acetyl-β-cyclodextrin can be prepared, for example, by reacting $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-β-cyclodextrin with an acetylating agent. The perfunctionalized cyclodextrin has been obtained in 90% yield by stirring the $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-β-cyclodextrin with acetic anhydride in pyridine at 40° C.

Analogously, $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-methylated-$3^A$, $3^B$, $3^C$, $3^D$, $3^E$, $3^F$, $3^G$-heptakis-O-methylated-β-cyclodextrin has been obtained in 65% yield by stirring with $CH_3I/DMF/NaH$ at 40° C. Also analogously, $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-phenylcarbamoyl-$3^A$, $3^B$, $3^C$, $3^D$, $3^E$, $3^F$, $3^G$-heptakis-O-phenylcarbamoyl-β-cyclodextrin has been prepared in 75% yield by stirring with phenyl isocyanate in pyridine at 80° C. This reaction can also be carried out with α- or β-naphthylisocyanate in place of the phenyl isocyanate.

For those embodiments of the invention in which amine groups, rather than azide groups, are present on the saccharide, azide-bearing saccharides can be prepared as described above and the azide groups then reduced to amine groups, for example by reaction with $LiAlH_4$. These can then be perfunctionalized if required.

The support material can be an inorganic material, for example silica gel, $Al_2O_3$, $TiO_2$ or $ZrO_2$, or a synthetic polymer material. In one embodiment the support material has free primary amine groups on its surface, to participate in the reaction that links the support material to the glucose moieties. The support material can be reacted with a primary amine-containing reagent to provide the required primary amine. For example silica gel can be reacted with an ω-aminoalkylene-trialkoxysilane, for example 3-aminopropyltrimethoxysilane, 3-aminopropyltriethoxysilane, 3-(2-aminoethyl) aminopropyltriethoxysilane or 3-(2-aminoethyl) aminopropyltrimethoxysilane. Aminised silica gel can be prepared according to the method of T. Hargitai et al. *J. Chromatogr.*, 1993, 628,11, giving the following composition as determined from elemental analysis: C, %3.25; H, %0.96; N, %0.98. The disclosure of Hargitai et al. is incorporated herein by reference.

As synthetic polymer materials that can be used as support material there are mentioned porous functional synthetic polymers, for example polymers of styrene copolymerised with another copolymerisable monomer, that bear an —$NH_2$ group or an —$N_3$ group, or bear a leaving group such as, for example, OH or a halogen, that can be replaced by an —$NH_2$ or —$N_3$ group. For instance, OH groups and halogen atoms can be replaced by $N_3$ by reaction with an alkali metal nitride, for example sodium, lithium or potassium nitride, in a polar solvent, for example dimethylformamide. Polymers of methyl methacrylate and such a copolymerisable monomer can also be used. As suitable copolymerisable monomers there are mentioned styrenes substituted in the benzene ring by aminoalkyl groups having, say, up to 6 carbon atoms. Examples include compounds of formula:

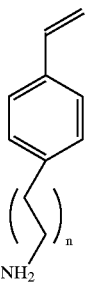

where n is 1, 2 or 3. Other suitable copolymerisable monomers include aminoalkyl esters of acrylic and methacrylic acid again having, say, up to 6 carbon atoms in the aminoalkyl group. Examples include compounds of formula:

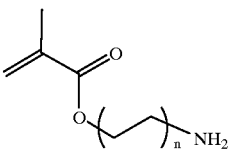

where n is 1, 2 or 3. Support materials bearing primary amine groups are commercially available.

A support material bearing azide groups can be prepared, for example, by reacting silica gel with an ω-haloalkylene-trialkoxysilane, followed by reaction with an alkali metal azide to replace the halogen atom with an azide group. As examples of ω-haloalkylene-trialkoxysilanes there are mentioned 3-bromopropyltrimethoxysilane, 3-bromopropyltriethoxysilane and the corresponding chloro compounds. As alkali metal azides there are mentioned sodium, potassium and lithium azides.

A support material bearing primary amine groups can be coupled directly to glucose moieties bearing azide groups to form a conjugate of the invention. In one procedure, the aminised support is stirred in a polar solvent, for example anhydrous tetrahydrofuran (THF) or anhydrous DMF, and $CO_2$ is passed continuously through the liquid. The azide-group-containing glucose reagent is added in the polar solvent following which a reactant for the Staudinger reaction, is added in the polar solvent. The reactant for the Staudinger reaction can be a trialkylphosphine for example a tri($C_{1-6}$-alkyl)phosphine, such as trimethylphosphine, or, preferably, triphenylphosphine. Corresponding trihydrocarbyloxy phosphines can also be used, for example a tri($C_{1-6}$-alkoxy)phosphine such as trimethoxyphosphine, or triphenoxyphosphine. Passage of $CO_2$ and stirring are continued to complete the reaction.

In another process for preparing the conjugate of the invention glucose moieties bearing azide groups are reacted with an alkenylamine, $CO_2$ and triphenylphosphine. The alkenylamine is preferably a straight-chained α-olefin with a primary amine attached to the ω-carbon atom. The number of carbon atoms is not critical, but is suitably in the range from 4 to about 22, i.e., the alkenylamine has the formula:

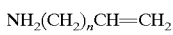
$NH_2(CH_2)_nCH=CH_2$ where n is a number in the range 2 to 20. 6-Aminohex-1-ene is mentioned as an example. Reaction occurs between azide groups, primary amine groups and $CO_2$ suitably under the conditions described above, resulting in compounds having urea linkages including nitrogen atoms of the azide groups and primary amines. Attached to the urea linkage is a hydrocarbyl group with an ω-alkenyl moiety. The reaction can be depicted schematically as follows:

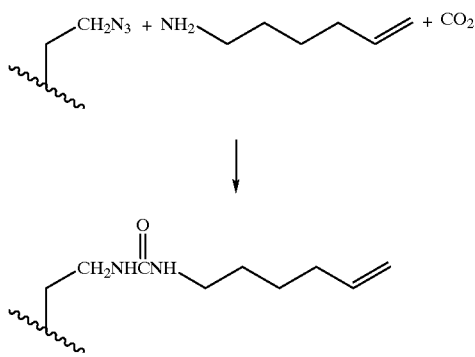

For those embodiments of the invention in which amine groups, rather than azide groups, are present on the saccharide, use is made of an alkenylazide corresponding to the alkenylamine described above, e.g. a compound of formula:

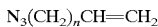
$N_3(CH_2)_nCH=CH_2$ where n is a number in the range 2 to 20. The reaction can be depicted schematically as follows:

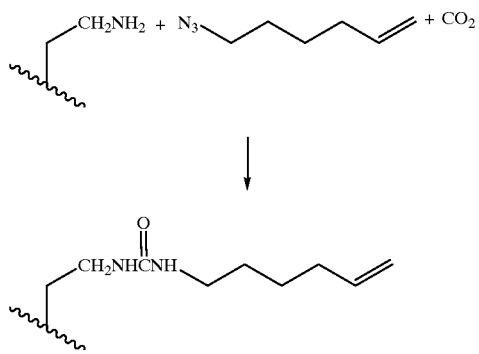

The alkenylazide reactant of formula:

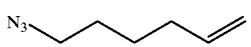

can be obtained by reacting the corresponding ω-haloalkene with an alkali metal azide.

The ω-alkenyl moiety is then hydrosilylated by reaction with, for example, a compound of formula:

$HSiR^1R^2R^3$ wherein each of $R^1$, $R^2$ and $R^3$ is an alkyl group or alkoxy group of up to 6 carbon atoms, an aryl or aryloxy group wherein the aryl moiety is a phenyl or α- or β-naphthyl group or a halogen atom (fluorine, chlorine, bromine or iodine), provided that at least one of $R^1$, $R^2$ and $R^3$ is a readily hydrolysable group such as an alkoxy or aryloxy group or a halogen atom. This compound adds to the alkenyl double bond, resulting in a group that can be schematically depicted as follows:

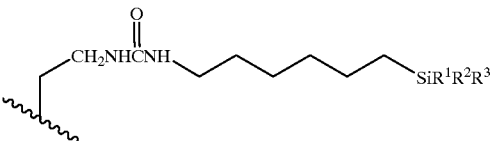

This group is then reacted with a support material, for example silica gel and the readily hydrolysable group bonds to the silica. For example, if the readily hydrolysable group is an alkoxy group there will be formed an Si—O—Si linkage to bind the cyclodextrin to the support material, with elimination of an alkanol.

In yet another process, glucose moieties bearing 6-azido groups are reacted with an aminosilane, for example a compound of formula:

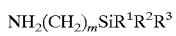
$NH_2(CH_2)_mSiR^1R^2R^3$ wherein m is an integer from 1 to about 20, $R^1$, $R^2$ and $R^3$ are defined above, and one or more methylene groups can be replaced by an oxygen atom or an imino group —NH—. Examples of such compounds include 3-aminopropyltrimethoxysilane, 3-aminopropyltriethoxysilane, 3-(2-aminoethyl)aminopropyltriethoxysilane and 3-(2-aminoethyl)aminopropyltrimethoxysilane. These compounds, $CO_2$ and triphenylphosphine are reacted under previously described conditions, to produce glucose moieties having attached to the 6-carbon atoms side chains having terminal Si atoms bearing a readily hydrolysable group. This can then be reacted with a support material, for example as described above, with formation of an Si—O—Si linkage and elimination of an alkanol.

For those embodiments of the invention in which amine groups, rather than azide groups, are present on the saccharide there can be used an azidosilane, for example a compound of formula:

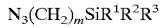
$N_3(CH_2)_mSiR^1R^2R^3$ wherein m, $R^1$, $R^2$ and $R^3$ are as defined above.

It will be appreciated from the above that although the cyclodextrin and support material are linked to each other via urea linkages, it is not necessary that one nitrogen atom of the urea moiety shall be attached directly to a carbon atom of the cyclodextrin and the other nitrogen atom of the urea moiety shall be attached directly to the support; the linkage can contain other moieties in addition to the urea moiety.

After the glucose moieties have been bound to the support material it is possible to treat the support material in an "end-capping" reaction in which reactive sites on the support material are protected. For instance, hydroxyl groups on silica gel can be reacted with a reactive silane such as, for example, trimethylchlorosilane or hexamethyldisilazane to block the surface hydroxyl groups.

Conjugates of the invention are particularly suitable for use in chromatography, for example high performance liquid chromatography (HPLC), liquid chromatography (LC), thin layer chromatography (TLC), capillary electrochromatography (CEC) and counter-current chromatography. The conjugates are particularly valuable as a chiral stationary phase (CSP) for resolving enantiomeric mixtures and in determining enantiomeric purity. The conjugates of the invention permit good reproducibility of separation, even after long run times in reverse phase separations using mobile phases having a high aqueous concentration. Their utility extends beyond use in chromatography, however. They can also be used for example in electrophoresis, especially chiral electrophoretic separations.

For use in chromatography it is preferred that the support material is in the form of spherical particles whose size is preferably from about 1 μm to about 20 μm, more preferably about 2 μm to 10 μm. For use in HPLC analytical separation a particle size of about 5 μm is preferred.

The invention is further illustrated in the following examples and in the accompanying drawings. Of the drawings:

BRIEF DESCRIPTON OF THE DRAWINGS

FIG. 2A shows the separation of enantiomers of propanolol using $H_2O$/acetonitrile 80/20 as the mobile phase.

$k_1=3.91$, $k_2=4.93$, $\alpha=1.27$, $R_s=2.61$.

Figure 1:
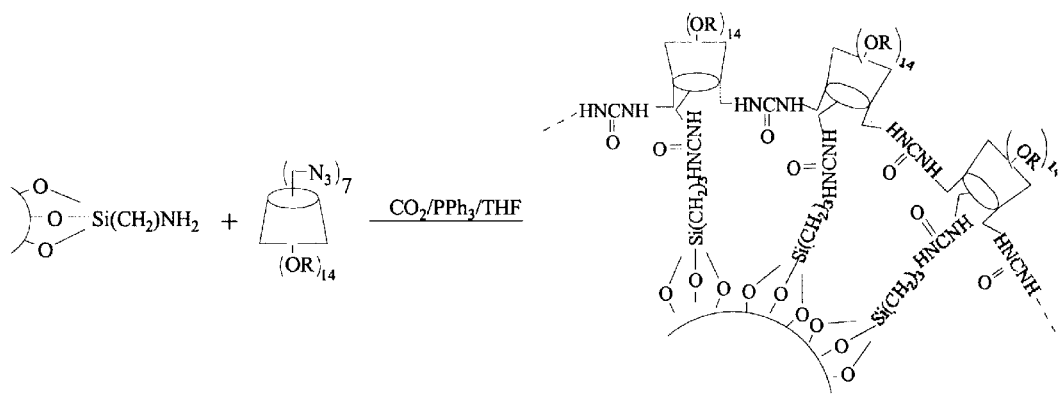
FIG. 1 shows schematically a synthesis in accordance with procedure (a), showing cyclodextrins that are bound to a support by linkages that include ureas and are also cross-linked by urea linkages.
Figure 2:
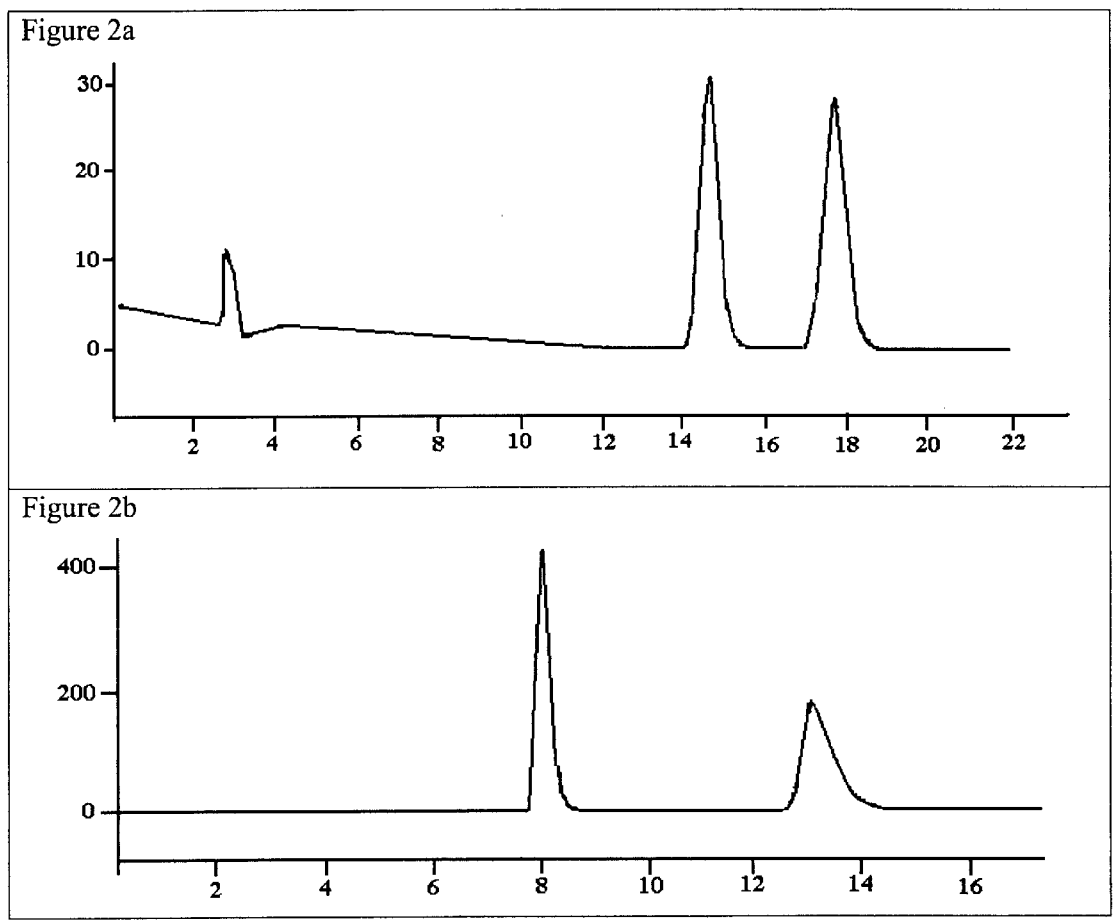
FIGS. 2A and 2B are chromatograms showing chiral separations using the product of Example 4.

FIG. 2B shows the separation of enantiomers of 1-parabromophenyl-ethanol using hexane/isopropanol (IPA) 90/10 s the mobile phase.

$k_1=1.38$, $k_2=3.40$, $\alpha=2.00$, $R_s=5.55$.

EXAMPLE 1

4 g of aminised silica gel, prepared by treatment of silica gel with 3-aminopropyltriethoxysilane, was stirred in 30 ml of anhydrous THF through which a continuous stream of $CO_2$ gas was passed. After 20 minutes, 1.2 g of $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-acetyl-$3^A$, $3^B$, $3^C$, $3^D$, $3^E$, $3^F$, $3^G$-heptakis-O-acetyl-β-cyclodextrin in 10 ml anhydrous THF was added. Stirring was continued for another 5 minutes, after which 2.0 g of triphenylphosphine in 20 ml of anhydrous THF was added. The mixture was stirred for 10 hours with constant bubbling of $CO_2$ at room temperature. The reaction mixture was then transferred to a soxhlet extraction apparatus and extracted with acetone for 24 hours. After removal of the acetone in vacuo, the peracetylated cyclodextrin cross-linked and immobilized on silica gel was obtained having the following composition as determined from elemental analysis: C, 12.46%; H, 1.97%; N, 1.03%.

EXAMPLE 2

4 g of aminised silica gel, prepared as described in Example 1, was stirred in 30 ml of anhydrous THF through which a continuous steam of $CO_2$ gas was passed. After 20 minutes, 1.2 g of $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-β-cyclodextrin in 30 ml of anhydrous DMF was added. Stirring was continued for another 5 minutes, after which 2.0 g of triphenylphosphine in 20 ml of anhydrous DMF was added. The mixture was stirred for 10 hours with constant bubbling of $CO_2$ at room temperature. After filtering through a glass frit and rinsing with pyridine, water, ethanol and petroleum ether (in this sequence), a cyclodextrin cross-linked and immobilized on silica gel was obtained having the following composition as determined from elemental analysis: C, 7.93%; H, 1.65%; N, 1.82%.

EXAMPLES 3 AND 4

The procedure of Example 1 was repeated using $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-methylated-$3^A$, $3^B$, $3^C$, $3^D$, $3^E$, $3^F$, $3^G$-heptakis-O-methylated-β-cyclodextrin (Example 3) or $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-phenylcarbamoylated-$3^A$, $3^B$, $3^C$, $3^D$, $3^E$, $3^F$, $3^G$-heptakis-O-phenylcarbamoylated-β-cyclodextrin (Example 4) in place of the $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-acetyl-β$3^A$, $3^B$, $3^C$, $3^D$, $3^E$, $3^F$, $3^G$-heptakis-O-acetyl-β-cyclodextrin of Example 1. The elemental analyses were as follows:

Example 3. Bonded with cross-linked permethylated-β-cyclodextrin: C, 11.45%; H, 1.85%; N, 1.14%.

Example 4. Bonded with cross-linked β-cyclodextrin perphenylcarbamate: C, 13.78%; H, 2.02%; N, 2.38%.

EXAMPLE 5

A solution of 9-decen-1-amine (0.08 g, 0.50 mmol) and $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-acetyl-$3^A$, $3^B$, $3^C$, $3^D$, $3^E$, $3^F$, $3^G$-heptakis-O-acetyl-β-cyclodextrin (0.90 g, 0.45 mmol) in 5 ml of anhydrous THF was stirred under a constant passage of dry $CO_2$ at room temperature. After 2 minutes, a solution of $PPh_3$ (0.12 g, 0.45 mmol) in 5 ml of anhydrous THF was added. This mixture was allowed to react for about 5 hours, after TLC revealed that no starting materials remained. After evaporation to dryness, the product was purified by column chromatography with ethyl acetate-acetone (1:1) as eluent in 90% yield.

EXAMPLES 6 AND 7

The procedure of Example 5 was repeated using $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-methylated-$3^A$, $3^B$, $3^C$, $3^D$, $3^E$, $3^F$, $3^G$-heptakis-O-methylated-β-cyclodextrin (Example 6) or $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-phenylcarbamoylated-$3^A$, $3^B$, $3^C$, $3^D$, $3^E$, $3^F$, $3^G$-heptakis-O-phenylcarbamoylated-β-cyclodextrin (Example 7) in place of the $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-acetyl-$3^A$, $3^B$, $3^C$, $3^D$, $3^E$, $3^F$, $3^G$-heptakis-O-acetyl-β-cyclodextrin of Example 5.

EXAMPLE 8

1.5 g of product obtained in Example 5 was stirred with 5 ml of triethoxysilane and 10 mg of tetrakis (triphenylphosphine) platinum (0) at 60° C. After 24 hours the mixture was adsorbed with 2 cm³ high molecular weight silica gel in a Buchner funnel and washed with 100 ml ether. After removal of the ether and volatiles by vacuum, the residue was dissolved in 50 ml anhydrous toluene, 4.0 g of silica gel (which had already been dried over vacuum at 120° C. overnight) was added, and the mixture was stirred at 80° C. for 8 hrs. 1 ml of water was added and the reaction was continued for another 3 hrs. After removing the volatiles, the residue was heated to 200° C. for 5 hrs. After filtering and extracting in a soxhlet apparatus with acetone for 24 hrs, a product with the following elemental analysis was obtained: C, 8.45%; H, 2.00%; N, 0.10%.

EXAMPLES 9 AND 10

The procedure of Example 8 was repeated using $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-methylated-$3^A$, $3^B$, $3^C$, $3^D$, $3^E$, $3^F$, $3^G$-heptakis-O-methylated-β-cyclodextrin (Example 9) or $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-penylcarbamoylated-$3^A$, $3^B$, $3^C$, $3^D$, $3^E$, $3^F$, $3^G$-heptakis-O-phenylcarbamoylated-β-cylodextrin (Example 10) in place of the $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-acetyl-$3^A$, $3^B$, $3^C$, $3^D$, $3^E$, $3^F$, $3^G$-heptakis-O-acetyl-β-cyclodextrin of Example 5 with elemental analyses shown as following:

Example 9. Bonded with cross-linked permethylated-β-cyclodextrin: C, 7.45%; H, 1.76%; N, 0.09%.

Example 10. Bonded with cross-linked β-cyclodextrin perphenylcarbamate: C, 9.03%; H, 2.03%; N, 0.25%.

EXAMPLE 11

Cellulose acetate (acetyl content: 30–40%) (5.0 g, 5.5 mmol as anhydroglucose, dried in vacuum at 90° C. overnight) and $LiN_3$ (1.47 g, 30 mmol) were dissolved in dried DMF (80 ml) at 90° C. under a nitrogen atmosphere and stirred for 2–2.5 hrs. after cooling to room temperature, a solution of Iodine (1.27 g, 5 mmol) and triphenylphosphine (1.57 g, 6 mmol) in dried DMF (30 ml) were then added and was stirred for 12 hrs at 90° C. under a nitrogen atmosphere throughout. After cooling to room temperature, methanol (3 ml) was added and the products were recovered by precipitation into ethanol. They were washed with ethanol and dried at 50–60° C. overnight.

The 6-azido-6-deoxy cellulose acetate was fully functionalized later on. A naphthylcarbamated derivative was prepared by heating with naphthylisocyanate in pyridine at 90° C. for 15 hours. An acetylated derivative was prepared by heating with acetic anhydride at 60° C. for 12 hours. A methylated derivative was prepared by reacting with methyl iodide in the presence of NaH and DMF at 25° C. for 12 hours.

EXAMPLE 12

The procedure of Example 1 was repeated with 6-azido-6-deoxy perfunctionalized cellulose in replace of the $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-heptakis-O-acetyl-$2^A$, $2^B$, $2^C$, $2^D$, $2^E$, $2^F$, $2^G$-heptakis-O-acetyl-β-cyclodextrin of Example 1.

EXAMPLE 13

The material produced in Example 4 was introduced into a column (250×4.6 mm). The column was used to separate various racemic compounds into their enantiomers and results are given in Table 1. Quite good chiral separation could be achieved both in normal phase and reverse phase. Peaks were detected by UV absorbance at 254 nm. A wide variety of chiral compounds and pharmaceutical active ingredients could be separated easily. A separation factor of more than 5 could be easily achieved for some drugs.

TABLE 1

Enantiomeric separation of various chiral compounds

| Substance | HPLC condition | Flow rate (ml/min) | Retention Time (in minutes) | α | Rs |
|---|---|---|---|---|---|
| Atropine | Condition 2 | 0.5 | 7.02/11.14 | 5.62 | 4.46 |
| Acebutalol | Condition 1 | 0.5 | 14.56/17.20 | 1.30 | 2.55 |
| Alprenolol | Condition 1 | 0.5 | 18.55/24.72 | 1.50 | 1.85 |
| Pindolol | Condition 1 | 0.5 | 11.72/13.60 | 1.34 | 1.21 |
| Isopreteralol | Condition 1 | 0.5 | 7.50/13.04 | 5.06 | 3.29 |
| Propranolol | Condition 5 | 1.0 | 22.50/38.83 | 1.43 | 1.52 |
| Bendroflumethiazide | Condition 3 | 0.5 | 25.50/36.10 | 1.49 | 3.19 |
| 4-methyl-4-phenyl Hydantoin | Condition 3 | 0.5 | 15.62/17.32 | 1.18 | 1.16 |
| p-bromo-phenyl ethanol | Condition 4 | 1.0 | 7.70/12.50 | 2.14 | 4.05 |

*Condition 1: MeOH/Buffer (98 mM TEAA, pH = 5.30) = 30/70 (v/v)
Condition 2: MeOH/Buffer (98 mM TEAA, pH = 4.67) = 50/50 (v/v)
Condition 3: MeOH/Water = 70/30 (v/v)
Condition 4: MeOH/IPA = 90/10 (v/v)
Condition 5: MeOH/IPA = 80/20 (v/v)

Conjugates prepared in accordance with the invention have been used as chiral stationary phase in chromatographic separation and have shown superiority to the product of U.S. Pat. No. 6,017,458, in which the cyclodextrin is linked to the support via a single urea linkage. For example, products of U.S. Pat. No. 6,017,458 can be used as stationary phase with a broad range of organic and organic/aqueous solvents. If the aqueous phase has a water content above 95%, however, there occurs an observable deterioration in the separation achieved. The conjugate of the present invention can be used with the same broad range of solvents as the product of U.S. Pat. No. 6,017,458. When used with an organic/aqueous solvent of 95% water content, however, the conjugate of the invention does not display observable deterioration and good results have been obtained up to a water content of 99.5%. Furthermore, using a conjugate of this invention it was possible to separate benzoin from dihydrobenzoin, whereas this was not possible with the product of U.S. Pat. No. 6,017,458.

Having now described the invention, it is not intended that it be limited except as may be required by the appended claims.

What is claimed is:

1. A conjugate comprising a support material linked to oligomers or polymers of a saccharide, which linking is via urea linkages between the saccharide moieties and the support material, and wherein the oligomers or polymers are also cross-linked via urea linkages.

2. A conjugate according to claim 1, wherein the saccharide is glucose.

3. A conjugate according to claim 2, wherein the oligomer or polymer of glucose is a cyclodextrin.

4. A conjugate according to claim 2, wherein the oligomer or polymer of glucose is β-cyclodextrin.

5. A conjugate according to claim 2, wherein the urea linkages are to the 6-carbon atoms of the glucose moieties.

6. A conjugate according to claim 2, wherein the linkages are to the 2-carbon atoms of the glucose moieties.

7. A conjugate according to claim 2, wherein the linkages are to the 3-carbon atoms of the glucose moieties.

8. A conjugate according to claim 1, wherein the oligomer or polymer of a saccharide is perfunctionalized by replacement of all free hydroxyl groups by a group selected from the group consisting of alkoxy groups, aryloxy groups, acyloxy groups and carbamoyloxy groups.

9. A conjugate according to claim 1, wherein the support material is selected from the group consisting of silica gel, $Al_2O_3$, $TiO_2$, $ZrO_2$ and, synthetic porous functional organic polymers bearing free —$NH_2$ moieties and synthetic porous functional organic polymers bearing free $N_3$ moieties.

10. A conjugate according to claim 9, wherein the support material is silica gel.

11. A process for preparing a conjugate according to claim 1, which process comprises:
(a) reacting an oligomer or polymer of a saccharide bearing a plurality of azide groups with an amine, a phosphine and $CO_2$, the amine being on the surface of a support material; or
(b) reacting an oligomer or polymer of a saccharide bearing a plurality of azide groups with an amine, a phosphine and $CO_2$, wherein the amine is an alkenylamine, subsequently hydrosilylating the alkenyl moiety of the product with a hydrosilylating agent that bears one or more readily hydrolysable groups on the silicon atom and thereafter reacting with a support member; or
(c) reacting an oligomer or polymer of a saccharide bearing a plurality of azide groups with an amine, a phosphine and $CO_2$, wherein the amine is present in a molecule that bears a silicon atom bearing at least one readily hydrolysable group, and thereafter reacting with a support member; or
(d) reacting an oligomer or polymer of a saccharide bearing a plurality of amine groups with an azide, a phosphine and $CO_2$, the azide being on the surface of a support material; or
(e) reacting an oligomer or polymer of a saccharide bearing a plurality of amine groups with an azide, a phosphine and $CO_2$, wherein the azide is an alkenylazide, subsequently hydrosilylating the alkenyl moiety of the product with a hydrosilylating agent that bears one or more readily hydrolysable groups on the silicon atom and thereafter reacting with a support member; or
(f) reacting an oligomer or polymer of a saccharide bearing a plurality of amine groups with an azide, a phosphine and $CO_2$, wherein the azide is present in a molecule that bears a silicon atom bearing at least one readily hydrolysable group, and thereafter reacting with a support member.

12. A process according to claim 11, wherein the saccharide is glucose.

13. A process according to claim 12, wherein the oligomer or polymer of a saccharide is perfunctionalized by replacement of all free hydroxyl groups by a functional group selected from the group consisting of alkoxy groups, aryloxy groups, acyloxy groups and carbamoyloxy groups.

14. A process according to claim 12, wherein the amine is a primary amine.

15. A process according to claim 12, wherein the phosphine is triphenylphosphine.

16. A process according to claim 11, wherein the oligomer or polymer of a saccharide is a cyclodextrin.

17. A process according to claim 11, wherein the oligomer or polymer of a saccharide is β-cyclodextrin.

18. A process according to claim 11, wherein the oligomer or polymer of a saccharide is a $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-β-cyclodextrin.

19. A process according to claim 18, wherein the oligomer or polymer of a saccharide is $6^A$, $6^B$, $6^C$, $6^D$, $6^E$, $6^F$, $6^G$-heptakisazido-$6^A$, $6^B$, $6^C$, $6^D$, $6^E$, $6^F$, $6^G$-heptakisdeoxy-$2^A$, $2^B$, $2^C$, $2^D$, $2^E$, $2^F$, $2^G$-O-phenylcarbamoylated-$3^A$, $3^B$, $3^C$, $3^D$, $3^E$, $3^F$, $3^G$-heptakis-O-phenylcarbamoylated-β-cyclodextrin.

20. A process according to claim 11, wherein the amine is a compound of formula $$NH_2(CH_2)_nCH=CH_2$$

wherein n is a number in the range 2 to 20, and the hydrosilylating agent is a compound of formula $$HSiR^1R^2R^3$$

wherein each $R^1$, $R^2$ and $R^3$ is an alkyl group or an alkoxy group of up to 6 carbon atoms, an aryl or aryloxy wherein the aryl moiety is a phenyl or α- or β-naphthyloxy group or a halogen atom provided that at least one of $R^1$, $R^2$ and $R^3$ is a readily hydrolysable group.

21. A process according to claim 11, wherein the amine is a compound of formula $$NH_2(CH_2)_mSiR^1R^2R^3$$

wherein m is a number from 1 to about 20 and each $R^1$, $R^2$ and $R^3$ is an alkyl group or an alkoxy group of up to 6 carbon atoms, an aryl or aryloxy wherein the aryl moiety is a phenyl or α- or β-naphthyloxy group or a halogen atom provided that at least one of $R^1$, $R^2$ and $R^3$ is a readily hydrolysable group.

22. A process according to claim 11, wherein the support material is selected from the group consisting of silica gel, $Al_2O_3$, $TiO_2$, $ZrO_2$ and synthetic porous functional organic polymers bearing free —$NH_2$ and —$N_3$ moieties.

23. A process according to claim 22, wherein the support material is silica gel.

* * * * *